US012642975B2

(12) United States Patent
Wisnoskey

(10) Patent No.: US 12,642,975 B2
(45) Date of Patent: Jun. 2, 2026

(54) METHOD AND SYSTEM FOR ADAPTIVE BI-VENTRICULAR FUSION PACING

(71) Applicant: Pacesetter, Inc., Sylmar, CA (US)

(72) Inventor: Brian Wisnoskey, Cleveland, CA (US)

(73) Assignee: Pacesetter, Inc., Sylmar, CA (US)

( * ) Notice: Subject to any disclaimer, the term of this patent is extended or adjusted under 35 U.S.C. 154(b) by 728 days.

(21) Appl. No.: 17/711,189

(22) Filed: Apr. 1, 2022

(65) Prior Publication Data

US 2022/0218999 A1 Jul. 14, 2022

Related U.S. Application Data

(63) Continuation of application No. 15/015,031, filed on Feb. 3, 2016, now Pat. No. 11,311,733.

(51) Int. Cl.
| | |
|---|---|
| *A61N 1/36* | (2006.01) |
| *A61N 1/365* | (2006.01) |
| *A61N 1/368* | (2006.01) |
| *A61N 1/372* | (2006.01) |

(52) U.S. Cl.
CPC ..... *A61N 1/36843* (2017.08); *A61N 1/36542* (2013.01); *A61N 1/3682* (2013.01); *A61N 1/37223* (2013.01); *A61N 1/37247* (2013.01); *A61N 1/3684* (2013.01); *A61N 1/36842* (2017.08)

(58) Field of Classification Search
CPC ................................. A61N 1/37; A61N 1/3712
See application file for complete search history.

(56) References Cited

U.S. PATENT DOCUMENTS

| | | | | |
|---|---|---|---|---|
| 6,058,328 | A | * 5/2000 | Levine | ............... A61N 1/36585 |
| | | | | 607/14 |
| 7,778,706 | B1 | 8/2010 | Min | |
| 8,442,634 | B2 | 5/2013 | Min | |
| 8,565,880 | B2 | 10/2013 | Dong | |
| 2004/0147966 | A1* | 7/2004 | Ding | ................... A61N 1/3627 |
| | | | | 607/9 |
| 2004/0193223 | A1 | 9/2004 | Kramer | |
| 2005/0209649 | A1 | 9/2005 | Petric | |
| 2006/0047320 | A1 | 3/2006 | Ping | |

(Continued)

FOREIGN PATENT DOCUMENTS

WO 2017074999 5/2017

OTHER PUBLICATIONS

European Search Report mailed Oct. 8, 2018; Application No. 18186494.3.

*Primary Examiner* — Michael J D'Abreu
(74) *Attorney, Agent, or Firm* — Dean D. Small; Carroll, Hoette & Butscher, LLC

(57) ABSTRACT

Methods and systems are provided for a rate adaptive bi-ventricular fusion pacing. The methods and systems deliver a first pulse at a left ventricular (LV) lead and a second pulse at a right ventricular (RV) lead based on a paced atrio-ventricular (AV) delay. The first pulse timed to be delivered concurrently with an intrinsic ventricular conduction. The methods and systems further repeat the delivery of the first pulse and the second pulse for a predetermined number of cycles. Additionally, the methods and systems measure an intrinsic AV conduction interval, and adjust the paced AV delay based on the intrinsic AV conduction interval and a negative hysteresis delta.

16 Claims, 6 Drawing Sheets

(56)                    References Cited

U.S. PATENT DOCUMENTS

| | | | |
|---|---|---|---|
| 2006/0235481 A1 | 10/2006 | Fogoros et al. | |
| 2006/0247698 A1* | 11/2006 | Burnes ................. | A61N 1/3627 |
| | | | 607/9 |
| 2008/0269826 A1* | 10/2008 | Lian ...................... | A61N 1/368 |
| | | | 607/30 |
| 2010/0069987 A1 | 3/2010 | Min | |
| 2010/0145405 A1* | 6/2010 | Min ................... | A61N 1/36842 |
| | | | 607/25 |
| 2010/0222834 A1 | 9/2010 | Sweeney et al. | |
| 2011/0098772 A1 | 4/2011 | Min | |
| 2011/0137369 A1 | 6/2011 | Ryu | |
| 2012/0165892 A1 | 6/2012 | Min | |
| 2013/0268017 A1* | 10/2013 | Zhang ................. | A61N 1/3627 |
| | | | 607/18 |

* cited by examiner

METHOD AND SYSTEM FOR ADAPTIVE BI-VENTRICULAR FUSION PACING

REFERENCE TO RELATED APPLICATIONS

The present application is a continuation application of, and claims priority to, U.S. application Ser. No. 15/015,031, Titled "METHOD AND SYSTEM FOR ADAPTIVE BI-VENTRICULAR FUSION PACING" which was filed on 3 Feb. 2016, the complete subject matter of which is expressly incorporated herein by reference in its entirety.

BACKGROUND OF THE INVENTION

Embodiments of the present disclosure generally relate to methods and system that provide for automatic, adaptive, and programmable bi-ventricular fusion pacing.

Implantable stimulation devices or cardiac pacemakers are a class of cardiac rhythm management devices that provide electrical stimulation in the form of pacing pulses to selected chambers of the heart. As the term is used herein, a pacemaker is any cardiac rhythm management device with a pacing functionality regardless of any additional functions it may perform, such as cardioversion/defibrillation.

A pacemaker is comprised of two major components, a pulse generator and a lead. The pulse generator generates the pacing stimulation pulses and includes the electronic circuitry and the power cell or battery. The lead, or leads, is implanted within the heart and has electrodes which electrically couples the pacemaker to the desired heart chamber(s). A lead may provide both unipolar and bipolar pacing and/or sensing configurations. In the unipolar configuration, the pacing pulses are generally applied (or responses are sensed) between an electrode carried by the lead and a case of the pulse generator or an electrode of another lead within the heart. In the bipolar configuration, the pacing pulses are applied (or responses are sensed) between a pair of electrodes carried by the same lead.

When the patient's own intrinsic rhythm fails, pacemakers can deliver pacing pulses to a heart chamber to induce a depolarization of that chamber, which is followed by a mechanical contraction of that chamber. For example, the pacemaker may deliver bi-ventricular (BiV) pacing pulses to the left ventricle (LV) and right ventricle (RV) of the heart. Conventionally, BiV pacing occurs at an expiration of a fixed atrio-ventricular (AV) delay that preempts a patient's intrinsic cardiac conduction to force BiV pacing therapy. Pacemakers further include sensing circuits that sense cardiac activity for the detection of intrinsic cardiac events such as intrinsic atrial depolarizations (detectable as P waves) and intrinsic ventricular depolarizations (detectable as R waves). By monitoring cardiac activity, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart. This therapy is referred to as cardiac resynchronization therapy (CRT).

However, some patients fail to respond to conventional CRT. Existing BiV pacing techniques do not adapt to changes in patient status. Thus, it becomes important to take into account changes in a patient's intrinsic conduction time, which can affect appropriate timing of the BiV pacing pulses. For example, the intrinsic conduction time of the patient can change in response to variations in heart rate, activity level (e.g., exercise), medications, clinical status, and/or the like. Additionally, existing BiV pacing techniques are not customizable to patient-specific timing.

Patients with wide QRS duration and left bundle branch block (LBBB) typically derive the most benefit from CRT. In addition, targeting the site of latest LV electrical activation with BiV pacing has been shown to be associated with reverse ventricular remodeling and quality of life improvements. These studies implicate that LV electrical dyssynchrony plays an important role in CRT response and taken together suggest a role for correction of electrical dyssynchrony in improving response to CRT using BiV fusion pacing. BiV fusion pacing corresponds to timing the BiV pacing pulse to arrive coincident with a patient's intrinsic right bundle conduction.

A need remains for improved methods and systems that automatically adjust the BiV fusion pacing parameters based on the intrinsic AV conduction and patient-specific timing.

SUMMARY

In accordance with embodiments herein a method is provided for a rate adaptive bi-ventricular fusion pacing. The method may deliver a first pulse at a left ventricular (LV) lead and a second pulse at a right ventricular (RV) lead based on a paced atrio-ventricular (AV) delay. The first pulse is timed to be delivered concurrently with an intrinsic ventricular conduction of the heart. The method may further repeat the delivery of the first pulse and the second pulse for a predetermined number of cycles. The method also may measure an intrinsic AV conduction interval, and adjust the paced AV delay based on the intrinsic AV conduction interval and a negative hysteresis delta. Additionally or alternatively, the negative hysteresis delta may be a user-defined programmable value.

In accordance with embodiments herein a system is provided for a rate adaptive bi-ventricular fusion pacing. The system may include a first pulse generator and a second pulse generator, and at least one processor. The system may also include a memory coupled to the at least one processor, wherein the memory stores program instructions. The program instructions are executable by the at least one processor to deliver a first pulse generated by the first pulse generator at a left ventricular (LV) lead and a second pulse generated by the second pulse generator at a right ventricular (RV) lead based on a paced atrio-ventricular (AV) delay. The first pulse is timed to be delivered concurrently with an intrinsic ventricular conduction. Additionally, the programmed instructions when executed by the at least one processor may further repeat the delivery of the first pulse and the second pulse for a predetermined number of cycles. Additionally, the programmed instructions when executed by the at least one processor may measure an intrinsic AV conduction interval, and adjust the paced AV delay based on the intrinsic AV conduction interval and a negative hysteresis delta.

DETAILED DESCRIPTION

Figure 1:
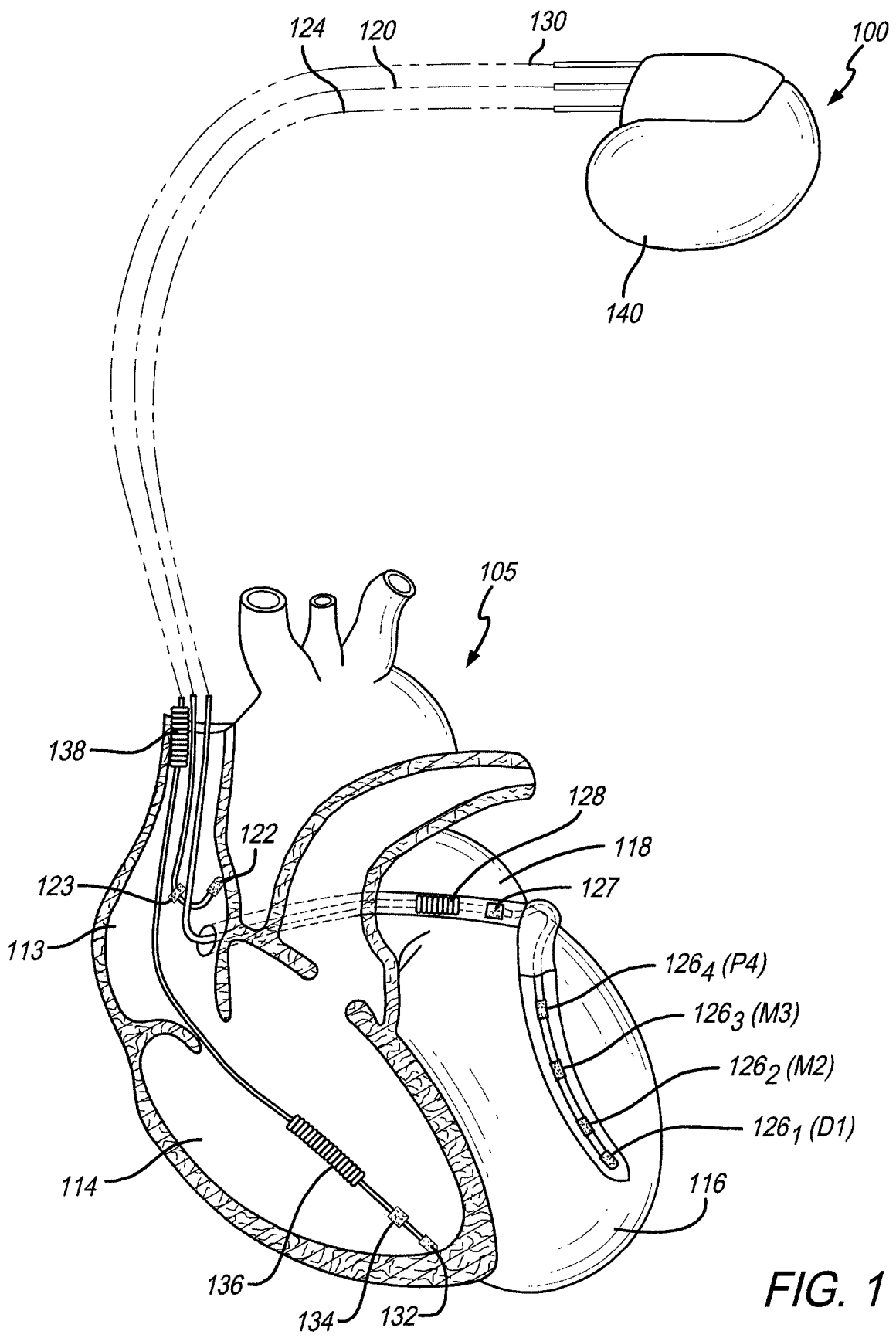
FIG. 1 illustrates an implantable medical device (IMD) in electrical communication with multiple leads implanted into a patient's heart for delivering multi-chamber stimulation and sensing cardiac activity, according to an embodiment.

The systems described herein can include or represent hardware and associated instructions (e.g., software stored on a tangible and non-transitory computer readable storage medium, such as a computer hard drive, ROM, RAM, or the like) that perform the operations described herein. The hardware may include electronic circuits that include and/or are connected to one or more logic-based devices, such as microprocessors, processors, controllers, or the like (collectively "processors"). These devices may be off-the-shelf devices that perform the operations described herein from the instructions described above. Additionally or alternatively, one or more of these devices may be hard-wired with logic circuits to perform these operations.

The foregoing summary, as well as the following detailed description of certain embodiments, will be better understood when read in conjunction with the appended drawings. To the extent that the FIGS. illustrate diagrams of the functional blocks of various embodiments, the functional blocks are not necessarily indicative of the division between hardware and circuitry. Thus, for example, one or more of the functional blocks (e.g., processors or memories) may be implemented in a single piece of hardware (e.g., a general purpose signal processor, microcontroller, random access memory, hard disk, and/or the like). Similarly, the programs may be standalone programs, may be incorporated as subroutines in an operating system, may be functions in an installed imaging software package, and the like. Furthermore, to the extent that the FIGS. illustrate flow diagrams of processes of various embodiments, the operations may be described by adding, rearranging, combining, or omitting the illustrated operations without departing from the scope of the processes as described herein. It should be understood that the various embodiments are not limited to the arrangements and instrumentality shown in the drawings.

One or more embodiments generally relate to implantable medical devices (IMDs) and systems such as pacemakers and implantable cardioverter-defibrillators that provide adaptive rate bi-ventricular (BiV) fusion pacing. At least one technical effect of various embodiments described herein if to continually reassess the intrinsic conduction of the patient and modify the timing of the BiV fusion pacing in a rate-adaptive fashion. BiV fusion pacing corresponds to BiV pacing stimuli that are timed to be delivered concurrently with the intrinsic ventricular events of the patient.

In accordance with embodiments herein, methods and systems periodically or continually measure an intrinsic atrio-ventricular (AV) conduction interval of a patient to identify any changes due to heart rate, activity level, cardiac conduction status, and/or the like of the patient. The BiV fusion pacing may be adjusted based on the measured AV conduction interval and a negative hysteresis algorithm, which may be configured by a user (e.g., clinician, doctor, medical technician). For example, the user may define parameters of the negative hysteresis algorithm during implantation and/or medical examination of the IMD based on echocardiography (ECHO) optimization, measurement of the QRS complex, and/or the like. Based on the programmable parameters, the negative hysteresis algorithm modifies the timing of the BiV fusion pacing and sets a rate responsive AV delay to match or "fuse" the intrinsic cardiac conduction of the patient and the BiV fusion pacing. In at least one embodiment, the Negative Hysteresis algorithm may set an interventricular pacing delay between the left ventricle (LV) and the right ventricle (RV).

FIG. 1 illustrates an implantable medical device (IMD) 100 in electrical communication with multiple leads implanted into a patient's heart 105 for delivering multichamber stimulation and sensing cardiac activity according to an embodiment. The IMD 100 may be a dual-chamber stimulation device, including an IMD, capable of treating both fast and slow arrhythmias with stimulation therapy, including cardioversion, defibrillation, and pacing stimulation, including cardiac resynchronization therapy (CRT). Optionally, the IMD 100 may be configured for single site or multi-site left ventricular (MSLV) pacing, which provides pacing pulses at more than one site within the LV chamber each pacing cycle. To provide atrial chamber pacing stimulation and sensing, the IMD 100 is shown in electrical communication with a heart 105 by way of a right atrial (RA) lead 120 having an atrial tip electrode 122 and an atrial ring electrode 123 implanted in the atrial appendage 113. The IMD 100 is also in electrical communication with the heart 105 by way of a right ventricular (RV) lead 130 having, in this embodiment, a ventricular tip electrode 132, an RV ring electrode 134, an RV coil electrode 136, and a superior vena cava (SVC) coil electrode 138. The RV lead 130 is transvenously inserted into the heart 105 so as to place the RV coil electrode 136 in the RV apex, and the SVC coil electrode 138 in the superior vena cava. Accordingly, the RV lead 130 is capable of receiving cardiac signals and delivering stimulation in the form of pacing and/or shock therapy to the right ventricle 114 (also referred to as the RV chamber).

To sense right atrial and ventricular cardiac signals and to provide left ventricle 116 (e.g., left chamber) pacing therapy, the IMD 100 is coupled to a multi-pole LV lead 124 designed for placement in various locations such as the "CS region", the epicardial space, etc. As used herein, the phrase "CS region" refers to the venous vasculature of the left ventricle, including any portion of the coronary sinus (CS), great cardiac vein, left marginal vein, left posterior ventricular vein, middle cardiac vein, and/or small cardiac vein or any other cardiac vein accessible by the coronary sinus. In an embodiment, an LV lead 124 is designed to receive atrial and ventricular cardiac signals and to deliver left ventricular pacing therapy using a set of multiple LV electrodes 126 that includes electrodes 126₁, 126₂, 126₃, and 126₄ (thereby providing a multipolar or multi-pole lead). The LV lead 124 also may deliver left atrial pacing therapy using at least an LA ring electrode 127 and shocking therapy using at least an LA coil electrode 128. In alternate embodiments, the LV lead 124 includes the LV electrodes 126₁, 126₂, 126₃, and 126₄, but does not include the LA electrodes 127 and 128. The LV lead 124 may be, for example, the Quartet™ LV pacing lead developed by St. Jude Medical Inc. (headquartered in St. Paul, Minn.), which includes four pacing electrodes on the LV lead. Although three leads 120, 124, and 130 are shown in FIG. 1, fewer or additional leads with various numbers of pacing, sensing, and/or shocking electrodes may optionally be used. For example, the LV lead 124 may have more or less than four LV electrodes 126.

When selecting a target venous branch for the LV lead 124, several factors may be taken into account. For example, it may be desirable to maximize the LV mass that may be captured by the LV lead 124. Accordingly, to maximize LV mass exposure, certain venous branches may be preferred for positioning the LV lead 124. Further, a diameter and trajectory of the venous branch is also considered to ensure that the venous branch will support chronic stability of an LV lead 124. Passive fixation of the LV lead 124 may be established through the anatomy of the host venous branch which causes the LV lead 124 to extend the distal portion thereof in a manner that differs from the LV lead's preformed shape. Optionally, additional factors to be considered when placing the LV lead 124 may include reducing myocardial capture thresholds, avoiding atrial and phrenic nerve stimulation, targeting site of latest LV electrical activation, and/or the like. After the LV lead 124 is positioned, the LV pacing vectors may be selected.

The LV electrode 126₁ (also referred to as D1) is shown as being the most "distal" LV electrode with reference to how far the electrode is from the left atrium 118. The LV electrode 126₄ (also referred to as P4) is shown as being the most "proximal" LV electrode 126 to the left atrium 118. The LV electrodes 126₂ and 126₃ are shown as being "middle" LV electrodes (also referred to as M2 and M3), between the distal and proximal LV electrodes 126₁ and 126₄, respectively. Accordingly, so as to more aptly describe their relative locations, the LV electrodes 126₁, 126₂, 126₃, and 126₄ may be referred to respectively as electrodes D1, M2, M3, and P4 (where "D" stands for "distal", "M" stands for "middle", and "P" stands from "proximal", and the numbers are arranged from most distal to most proximal, as shown in FIG. 1). Optionally, more or fewer LV electrodes may be provided on the lead 124 than the four LV electrodes D1, M2, M3, and P4.

The LV electrodes 126 are configured such that each electrode may be utilized to deliver pacing pulses and/or sense pacing pulses (e.g., monitor the response of the LV tissue to a pacing pulse). In a pacing vector or a sensing vector, each LV electrode 126 may be controlled to function as a cathode (negative electrode). Pacing pulses may be directionally provided between electrodes to define a pacing vector. In a pacing vector, a generated pulse is applied to the surrounding myocardial tissue through the cathode. The electrodes that define the pacing vectors may be electrodes in the heart 105 or located externally to the heart 105 (e.g., on a housing/case device 140). For example, the housing/case 140 may be referred to as the CAN and function as an anode in unipolar pacing and/or sensing vectors. The RV coil 136 may also function as an anode in unipolar pacing and/or sensing vectors. The LV electrodes 126 may be used to provide various different vectors. Some of the vectors are intraventricular LV vectors (e.g., vectors between two of the LV electrodes 126), while other vectors are interventricular vectors (e.g. vectors between an LV electrode 126 and the RV coil 136 or another electrode remote from the left ventricle 116). Below is a list of exemplary bipolar sensing vectors with LV cathodes that may be used for sensing using the LV electrodes D1, M2, M3, and P4 and the RV coil 136. In the following list, the electrode to the left of the arrow is assumed to be the cathode, and the electrode to the right of the arrow is assumed to be the anode.

D1→RV coil
M2→RV coil
M3→RV coil
P4→RV coil
D1→M2
D1→P4
M2→P4
M3→M2

6

M3→P4
P4→M2

It is recognized that various other types of leads and IMDs may be used with various other types of electrodes and combinations of electrodes. The foregoing electrode types/combinations are provided as non-limiting examples. Further, it is recognized that utilizing an RV coil electrode as an anode is merely one example. Various other electrodes may be configured as the anode electrode. Below is a list of exemplary bipolar pacing vectors with LV cathodes that may be used for pacing using the LV electrodes D1, M2, M3, and P4 and the RV coil 136. In the following list, the electrodes to the left of the arrow are assumed to be cathodes, and the electrode to the right of the arrow is assumed to be the anode.

D1→RV coil (or CAN)+M2→RV coil (or CAN)
M2→RV coil (or CAN)+M3→RV coil (or CAN)
M3→RV coil (or CAN)+M4→RV coil (or CAN)
M2→RV coil (or CAN)+M3→RV coil (or CAN)+ P4→RV coil (or CAN)
D1→RV coil (or CAN)+M2→RV coil (or CAN)+ M3→RV coil (or CAN)

It is noted that the preceding list is only a subset of the available pacing and sensing vectors for use with the IMD 100. Further, when delivering a series of pacing pulses, one of the above pacing vectors is used for at least the first pacing pulse in the series. Other pacing vectors may be used for subsequent pulses in the series of pacing pulses. Furthermore, additional pacing pulses may be generated in other chambers of the heart, such as the right ventricle.

Figure 2:
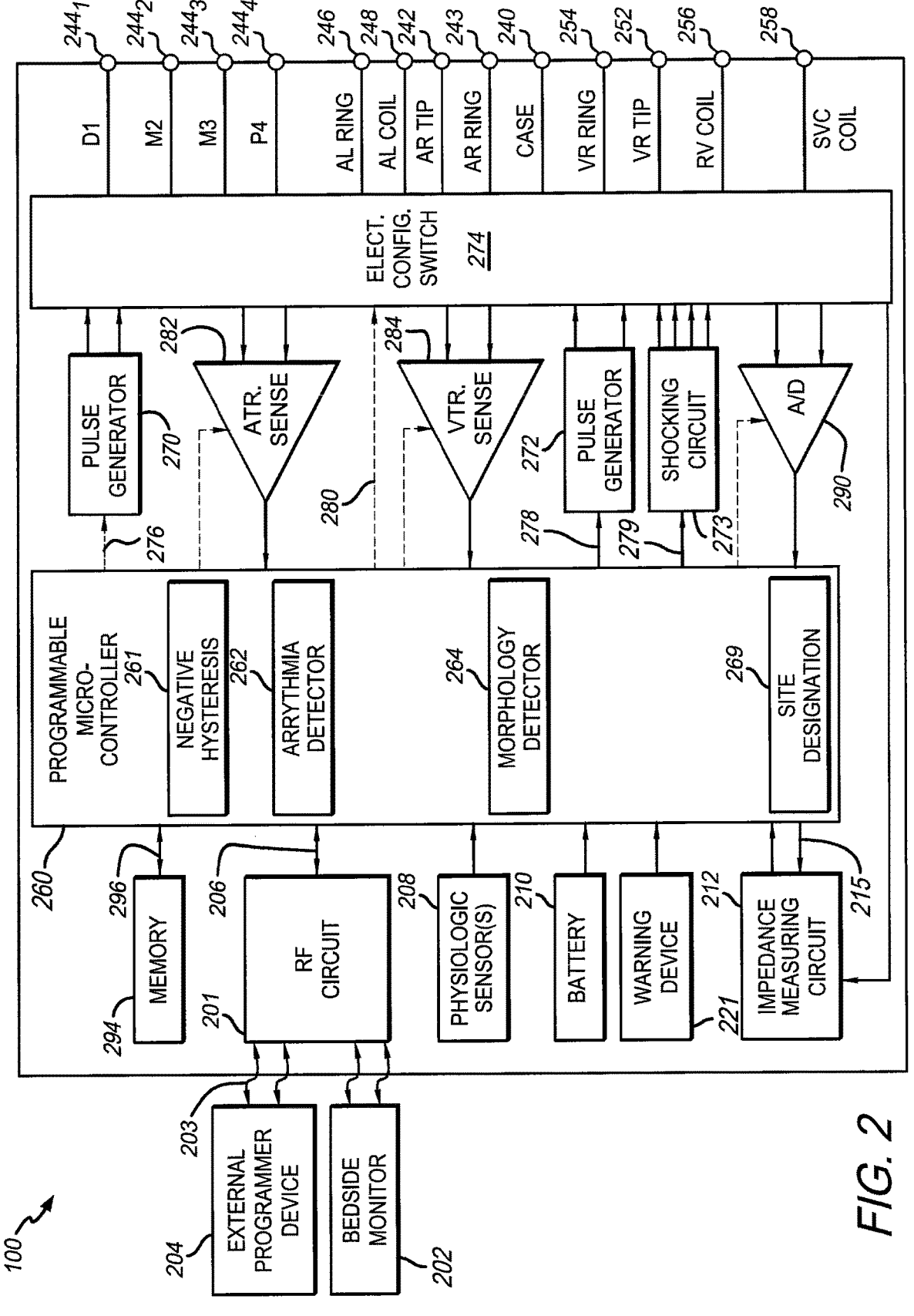
FIG. 2 illustrates a simplified block diagram of internal components of the IMD shown in FIG. 1, according to an embodiment.

FIG. 2 illustrates a simplified block diagram of internal components of the IMD 100 according to an embodiment. While a particular IMD 100 is shown, it is for illustration purposes only. One of skill in the art could readily duplicate, eliminate, or disable the appropriate circuitry in any desired combination to provide a device capable of treating the appropriate chamber(s) with cardioversion, defibrillation, and pacing stimulation. The housing/CAN 240 for IMD 100, shown schematically in FIG. 2 may be programmably selected to act as the anode for at least some unipolar modes. The CAN 240 may further be used as a return electrode alone or in combination with one or more of the coil electrodes 128, 136, and 138 (all shown in FIG. 1) for shocking purposes.

The IMD 100 further includes a connector (not shown) having a plurality of terminals, 242, 243, 244₁-244₄, 246, 248, 252, 254, 256, and 258 (shown schematically and, for convenience, with the names of the electrodes to which they are connected). As such, to achieve right atrial (RA) sensing and pacing, the connector includes at least an RA tip terminal (A_R TIP) 242 adapted for connection to the atrial tip electrode 122 (shown in FIG. 1) and an RA ring (A_R RING) electrode 243 adapted for connection to the RA ring electrode 123 (shown in FIG. 1). To achieve left chamber sensing, pacing, and shocking, the connector includes an LV tip terminal 244₁ adapted for connection to the D1 electrode and additional LV electrode terminals 244₂, 244₃, and 244₄ adapted for connection to the M2, M3, and P4 electrodes, respectively, of the quadripolar LV lead 124 (shown in FIG. 1). The connector also includes an LA ring terminal (A_L RING) 246 and an LA shocking terminal (A_L COIL) 248, which are adapted for connection to the LA ring electrode 127 (shown in FIG. 1) and the LA coil electrode 128 (shown in FIG. 1), respectively. To support right chamber sensing, pacing, and shocking, the connector further includes an RV tip terminal (V_R TIP) 252, an RV ring terminal (V_R RING) 254, an RV coil terminal (RV COIL) 256, and an SVC coil terminal (SVC COIL) 258, which are adapted for connection to the RV tip electrode 132, the RV ring electrode 134, the RV coil electrode 136, and the SVC coil electrode 138 (all four electrodes shown in FIG. 1), respectively.

At the core of the IMD 100 is a controller circuit 260, which controls the various modes of stimulation therapy. The controller circuit 260 (also referred to herein as a control unit or controller) may include one or more processors, a microprocessor or equivalent control circuitry, designed specifically for controlling the delivery of stimulation therapy. In at least one embodiment, the controller circuit 260 may be a microcontroller. The controller circuit 260 may further include RAM or ROM memory, logic and timing circuitry, state machine circuitry, and/or I/O circuitry. The controller circuit 260 includes the ability to process or monitor input signals (data) as controlled by a program code stored in a designated block of memory. The details of the design and operation of the controller circuit 260 are not critical to the invention. Rather, any suitable controller circuit 260 may be used that carries out the functions described herein. Among other things, the controller circuit 260 receives, processes, and manages storage of digitized cardiac data sets from the various sensors and electrodes.

A pulse generator 270 and a pulse generator 272 are configured to generate and deliver a pacing pulse from at least one RV or RA pacing site, such as at one or more pacing sites along the RA lead 120, the RV lead 130, and/or the LV lead 124 (all three leads shown in FIG. 1). For example, the pulse generator 270 generates pulses for delivery by the RA lead 120 and/or RV lead 130, while the pulse generator 272 generates pulses for delivery by the LV lead 124. The pacing pulses are routed from the pulse generators 270, 272 to selected electrodes within the leads 120, 124, 130 through an electrode configuration switch 274. It is understood that in order to provide stimulation therapy in each of the four chambers of the heart, the pulse generators 270 and 272, may include dedicated, independent pulse generators, multiplexed pulse generators, or shared pulse generators. The pulse generators 270, 272 are controlled by the controller circuit 260 via appropriate control signals 276, 278, respectively, to trigger or inhibit the stimulation pulses, including the timing and output of the pulses.

The pulse generators 270, 272 deliver, in connection with measuring the base capture threshold, successive stimulation pulses that have different stimulation amplitudes starting at an upper limit of the outer test range and decreasing by predetermined amounts. The pulse generators 270, 272 deliver, in connection with measuring the secondary capture threshold, one or more pacing pulses having stimulation amplitudes that vary over the inner test range.

Optionally, the pulse generators 270, 272 deliver one or more pacing pulses beginning with an initial stimulation amplitude having a voltage that is lower than a voltage of an initial stimulation amplitude associated with the outer test range used to measure the base capture threshold. The pulse generators 270, 272, in connection with measuring the base and secondary capture thresholds, begin at first and second outer voltages corresponding to one of the limits of the outer and inner test ranges, respectively, the first and second outer voltages differing from one another.

The electrode configuration switch 274 may include a plurality of switches for connecting the desired electrodes to the appropriate I/O circuits, thereby providing complete electrode programmability. Accordingly, the switch 274, in response to a control signal 280 from the controller circuit 260, controls the polarity of the stimulation pulses (e.g., unipolar, bipolar, etc.) by selectively actuating the appropriate combination of switches (not shown) as is known in the art. The switch 274 also switches among the various LV electrodes 226 to select the channels (e.g., vectors) to deliver and/or sense one or more of the pacing pulses. As explained herein, the switch 274 couples multiple LV electrode terminals $244_1$-$244_4$ correspond to cathodes when connected to the pulse generator 272.

Atrial sensors or sensing circuits 282 and ventricular sensors or sensing circuits 284 may also be selectively coupled to the RA lead 120, the LV lead 124, and/or the RV lead 130 (all three leads shown in FIG. 1) through the switch 274. The atrial and ventricular sensors 282 and 284 have the ability to detect the presence of cardiac activity in each of the four chambers of the heart 105 (shown in FIG. 1). For example, the atrial sensors 282 is configured to sense AV conduction of the patient. Optionally, the ventricular sensor 284 is configured to sense LV activation events at multiple LV sensing sites, such as the intrinsic cardiac conduction of the LV 116 and/or activation events generated in response to a pacing pulse.

The atrial sensing circuits 282 and ventricular sensing circuits 284 may include dedicated sense amplifiers, multiplexed amplifiers, or shared amplifiers. The switch 274 determines the "sensing polarity" or sensing vector of the cardiac signal by selectively opening and/or closing the appropriate switches, as is known in the art. In this way, a clinician may program the sensing polarity independent of the stimulation polarity. The outputs of the atrial and ventricular sensing circuits 282 and 284 are connected to the controller circuit 260. The outputs, in turn, are able to trigger or inhibit the atrial and ventricular pulse generators 270 and 272, respectively, in a demand fashion in response to the absence or presence of cardiac activity in the appropriate chambers of the heart 105.

Cardiac signals are also applied to the inputs of an analog-to-digital (ND) data acquisition system 290. The A/D data acquisition system 290 is configured to acquire intracardiac electrogram (IEGM) signals, convert the raw analog data into a digital signal, and store the digital signals for later processing and/or telemetric transmission. The telemetric transmission may be to an external programmer 204, a bedside monitor, and/or a personal advisory module (PAM) 202. The data acquisition system 290 may be operatively coupled to the RA lead 120, the LV lead 124, and the RV lead 130 (all three leads shown in FIG. 1) through the switch 274 to sample cardiac signals across any pair of desired electrodes.

The controller circuit 260 controls the actual delivery of CRT pacing pulses to synchronize the contractions of the right and left ventricles. For example, the CRT pacing pulses may be BiV fusion pacing delivered by the IMD 100 concurrently and/or simultaneously with the intrinsic ventricular events of the heart 105. The controller circuit 260 controls the number, timing, and output of the CRT pacing pulses delivered during each cardiac cycle by utilizing a negative hysteresis module 261 of the controller circuit 260.

In various embodiments, the negative hysteresis module 261 may be a negative hysteresis algorithm executed by the controller circuit 260. The negative hysteresis module 261 may control the timing of the CRT pacing pulses, including, but not limited to, pacing rate, atrio-ventricular (AV) delay, interatrial conduction delay, interventricular conduction delay, and/or intraventricular pacing delay. For example, the negative hysteresis module 261 may instruct the pulse generators 270, 272 when to deliver the pacing pulses to the switch 274 for the LV 116 or the RV 114. The negative hysteresis module 265 controls the timing of the CRT pacing pulses to be delivered to the LV lead 124 concurrently and/or simultaneously with the intrinsic cardiac conduction of the RV 114, which configures the CRT pacing pulses to BiV fusion pacing. For example, in connection with FIG. 3, the negative hysteresis module 265 may time the CRT pacing pulses based on an intrinsic AV conduction interval 314 and a negative hysteresis delta.

Figure 3:
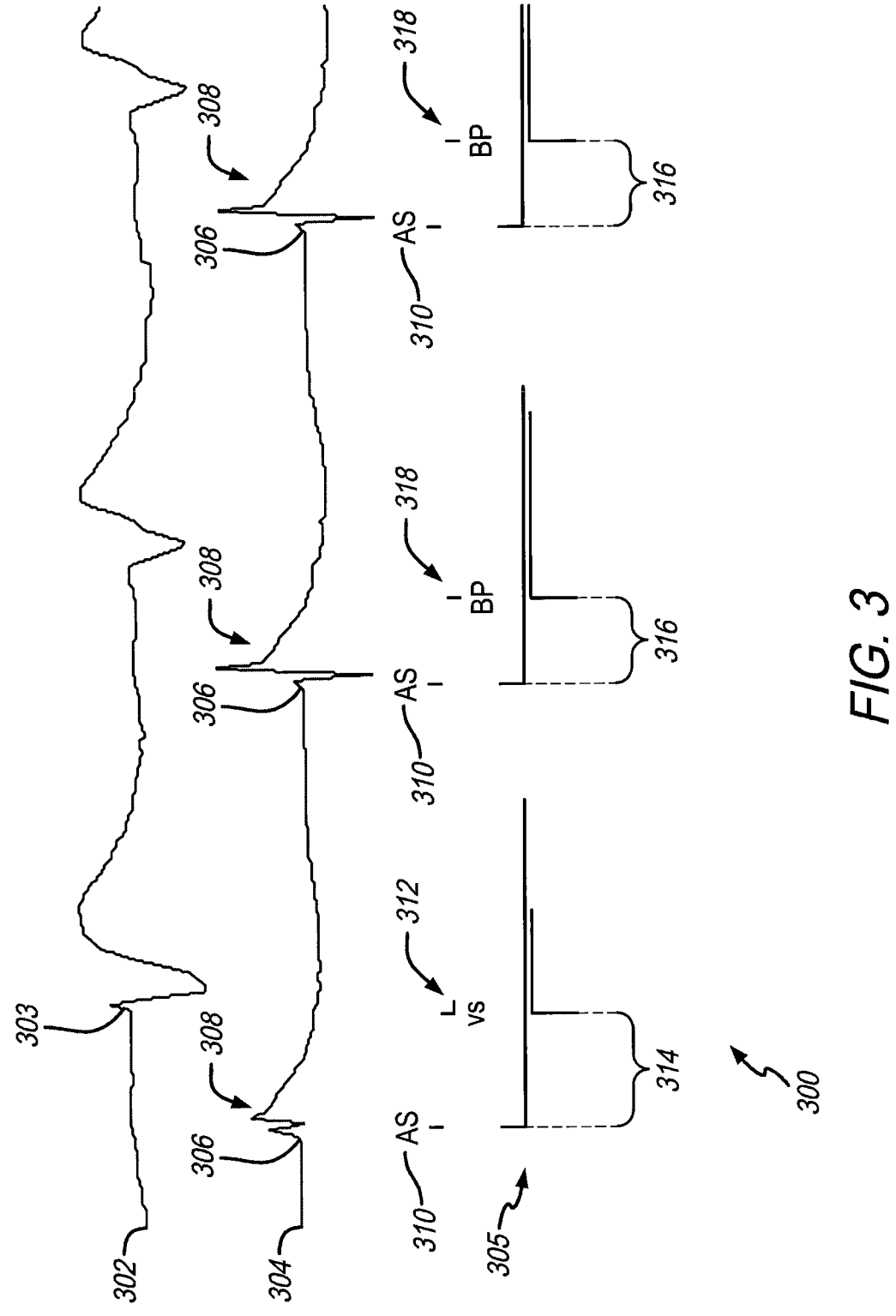
FIG. 3 illustrates electrocardiography and pacing delay data, according to an embodiment.

FIG. 3 illustrates electrocardiography and pacing delay data 300 in accordance with an embodiment. The illustrated electrocardiography data includes a heart electrocardiogram 302 and an atrial electrocardiogram 304. The heart electrocardiogram 302 and the atrial electrocardiogram 304 may have been acquired by the atrial sensing circuit 282 and/or the ventricular sensing circuits 284, shown in FIG. 2, of the IMD 100.

The atrial electrocardiogram 304 may be used by the negative hysteresis module 261 to identify intrinsic atrial conductions 308 of the heart 105. For example, the intrinsic atrial conductions 308 may include a series of peaks measured by the atrial sensing circuit 282. The negative hysteresis module 261 may identify a start 306 of the intrinsic atrial conduction 308 based on changes in slope of the atrial electrocardiogram 304. For example, when the negative hysteresis module 261 detects a change in the slope of the atrial electrocardiogram 304 above a predetermined threshold, the negative hysteresis module 261 may determine that the change of slope corresponds to a start 306 of the intrinsic atrial conduction 308 of the heart 105.

The heart electrocardiogram 302 may be used by the negative hysteresis module 261 to identify an intrinsic ventricular conduction 303 (e.g., ventricular sense) of the heart 105. Additionally or alternatively, the ventricular sense amplifier 284 may be used by the negative hysteresis module to identify an intrinsic ventricular conduction 303 of the heart 105. The negative hysteresis module 261 may identify the intrinsic ventricular event conduction 303 based on changes in slope of the heart electrocardiogram 302. For example, when the negative hysteresis module 261 detects a change in the slope of the heart electrocardiogram 302 above a predetermined threshold, the negative hysteresis module 261 may determine that the change of slope corresponds to the intrinsic ventricular event conduction 303 of the heart 105.

Timing data of the intrinsic atrial events conductions 308 and the intrinsic ventricular conduction 303, for example determined by the negative hysteresis module 261, are illustrated in the pacing delay data 305. The start 306 of the intrinsic atrial conduction 308 may be represented by the AS indicator 310 (e.g., atrial sense). The intrinsic ventricular conduction 303 (also referred to as an intrinsic ventricular event) is represented by the VS indicator 312 (e.g., ventricular sense). The intrinsic AV conduction interval 314 represents an amount of time from the start 306 of the intrinsic atrial conduction 308 and the intrinsic ventricular conduction 303. For example, the intrinsic AV conduction interval 314 corresponds to a length of time the intrinsic ventricular conduction 303 occurs after the intrinsic atrial conduction 308. Based on the intrinsic AV conduction interval 314, the negative hysteresis module 261 may determine a paced AV delay 316.

The paced AV delay 316 determines when the IMD 100 delivers BiV fusion pacing, shown as BP 318 in FIG. 3, after or subsequent to the start 306 of the intrinsic atrial event conduction 308 (e.g., the AS indicator 310). For example, the paced AV delay 316 defines a period of time starting at the start 306 of the intrinsic atrial conduction 308 and ending at the BiV fusion paced event, BP 318. The paced AV delay

316 is calculated or defined by the negative hysteresis module 261 based on the intrinsic AV conduction interval 314 and a negative hysteresis delta. The negative hysteresis delta may be a programmable value that is programmable by a user (e.g. physician, clinician, etc.) and stored in the memory 294. In various embodiments, the negative hysteresis delta may be between ten and one hundred twenty milliseconds.

The negative hysteresis delta is configured to adjust a time at which the IMD 100 delivers the BiV fusion pacing in order to stimulate the LV 116 concurrently and/or simultaneously with the intrinsic conduction of the RV 114. For example, the negative hysteresis delta is used to define the paced AV delay 316 to be less than or shorter than the intrinsic AV conduction interval 314. The length of the paced AV delay 316 allows the BiV fusion pacing to support and/or occur with the intrinsic conduction of the heart 105. Defining the paced AV delay 316 to be less than the intrinsic AV conduction interval 314 increases a likelihood that the BiV fusion pacing delivered by the IMD 100 is not pre-empted by the intrinsic conduction of the heart 105.

In at least one embodiment, the negative hysteresis module 261 that may calculate the paced AV delay based on Equation 1 shown below.

$$\text{Paced AV delay=intrinsic AV conduction interval–Negative Hysteresis Delta} \quad \text{(Equation 1).}$$

For example, the negative hysteresis module 261 may determine the intrinsic AV conduction interval 314 is 160 milliseconds. The negative hysteresis module 261 may subtract, from the intrinsic AV conduction interval 314, the negative hysteresis delta corresponding to, for example, 50 milliseconds as shown in Equation 1. Based on the AV conduction interval 314 and the negative hysteresis delta, the negative hysteresis module 261 may define the paced AV delay 316 to be 110 milliseconds.

Additionally or alternatively, the negative hysteresis module 261 may continually monitor the heart electrocardiogram 302 after or subsequent to defining the paced AV delay 316. For example, the negative hysteresis module 261 may monitor the heart electrocardiogram 302 to determine if subsequent intrinsic ventricular conduction occurs prior to an end of (e.g., within, during) the paced AV delay 316 or pre-empts the BP 318. For example, the intrinsic ventricular conduction can change based on changes in the heart rate, changes in activity level of the patient, medication taken by the patient, and/or the like. When the intrinsic conduction of the heart 105 pre-empts the BiV pacing, the IMD 100 may not deliver BiV fusion pacing to the LV 116 and/or RV 114. Additionally, the negative hysteresis module 261 may automatically adjust or redefine the paced AV delay 316 based on the detected subsequent intrinsic ventricular conduction.

For example, the negative hysteresis module 261 may define an adjusted AV conduction interval based on the subsequent intrinsic ventricular conduction. Based on the adjusted AV conduction interval and the negative hysteresis delta, the negative hysteresis module 261 may define a new or second paced AV delay. The new paced AV delay determined by the negative hysteresis module 261 additionally adjusts the delivery of the BiV fusion pacing by the IMD 100. Thereby, the negative hysteresis module 261 provides adaptive BiV fusion pacing by adjusting the delivery of the BiV fusion pacing, BP 318, based on changes in the intrinsic conduction of the heart 105.

Optionally, the negative hysteresis module 261 may adjust or reassess the paced AV delay 316 at a measurement cycle. The measurement cycle represents a delay prior to the negative hysteresis module 261 measuring a new intrinsic AV conduction interval 314 to define a new paced AV delay. For example, the measurement cycle may occur after a predetermined number of cycles, which is stored in the memory 294. The predetermined number of cycles may correspond to a number of consecutively paced AV delays 316 or BiV fusion pacing pulses delivered by the IMD 100.

For example, the measurement cycle may occur on the 32nd cycle after or subsequent to the IMD 100 delivering 31 consecutive BiV fusion pacing pulses to the LV 116 and the RV 114. On the 32nd cycle, the measurement cycle, the negative hysteresis module 261 may measure the intrinsic conduction of the heart 105. For example, on the 32nd cycle, the IMD 100 may not deliver a BiV fusion pacing pulses. The negative hysteresis module 261 measures the intrinsic ventricular conduction (e.g., the intrinsic ventricular conduction 303) of the heart 105, and calculates a new intrinsic AV conduction interval (e.g., the intrinsic AV conduction interval 314). Based on the new intrinsic AV conduction interval and the negative hysteresis delta, the negative hysteresis module 261 calculates (e.g., utilizing Equation 1) a new or adjusted paced AV delay.

Additionally or alternatively, the negative hysteresis module 261 may reassess or adjust the paced AV delay based on more than one intrinsic AV conduction interval. The negative hysteresis module 261 may be configured to measure a plurality of intrinsic AV conduction intervals during a reassessment period. The reassessment period may correspond to a plurality of consecutive cycles (e.g., consecutive paced AV delays 316, consecutive BiV fusion pacing pulses). For example, the reassessment period may correspond to five cycles. It may be noted in other embodiments the reassessment period may include more than five cycles or less than five cycles. During the reassessment period, the IMD 100 may not deliver the BiV fusion pacing pulses, and the negative hysteresis module 261 may measure a series of intrinsic AV conduction intervals. The negative hysteresis module 261 may calculate an average or mean intrinsic AV conduction interval from the series of intrinsic AV conduction intervals acquired during the reassessment period. The mean intrinsic AV conduction may take into account recovery time and increase the accuracy of the overall intrinsic conduction time measurement by reducing the effect of outlying intrinsic AV conduction measurements. The negative hysteresis module 261 may calculate a new or adjusted paced AV delay based on the mean intrinsic AV conduction interval and the negative hysteresis delta.

Optionally, the new or adjusted paced AV delay defined subsequent to the measurement cycle may be continually adjusted or reassessed after a BiV pacing cycle. The BiV pacing cycle may include a predetermined number of cycles. The BiV pacing cycle may be a series of consecutive BiV fusion pacing pulses delivered by the IMD 100 prior to the negative hysteresis module 261 measuring a new intrinsic AV conduction interval 314. The predetermined number of cycles may be stored in the memory 294.

For example, the BiV pacing cycle may be 256 cycles corresponding to the IMD 100 delivering BiV fusion pacing 255 consecutive times to the LV 116 and the RV 114. On the 256th cycle, the negative hysteresis module 261 may measure the intrinsic conduction of the heart 105. For example, on the 256th cycle, the IMD 100 may not deliver BiV fusion pacing. The negative hysteresis module 261 measures an intrinsic ventricular conduction (e.g., the intrinsic ventricular conduction 303) of the heart 105, and calculates a new intrinsic AV conduction interval (e.g., the intrinsic AV conduction interval 314). Based on the new intrinsic AV conduction interval and the negative hysteresis delta, the negative hysteresis module 261 may calculate (e.g., utilizing Equation 1) a paced AV delay (e.g., the paced AV delay 316). In various embodiments, the negative hysteresis module 261 may continually transition from the measurement cycle and the BiV pacing cycle. By reassessing or adjusting the paced AV delay during the measurement cycle and the BiV pacing cycle, the negative hysteresis module 261 provides a rate-adaptive BiV fusion pacing in patients with intact AV conduction and LBBB.

Additionally or alternatively, the negative hysteresis module 261 may include an interventricular pacing delay between the LV 116 and the RV 114. The interventricular pacing delay may correspond to a difference in time between the BiV fusion paced delivered to the LV 116 and the BiV fusion pacing pulses delivered to the RV 114. Optionally, the negative hysteresis module 261 may keep track of the timing of refractory periods, blanking intervals, noise detection windows, evoked response detection windows, alert intervals, marker channel timing, and/or the like, which is known in the art.

Returning to FIG. 2, the controller circuit 260 further includes an arrhythmia detector 262 for operating the IMD 100 as an implantable cardioverter/defibrillator device. The detector 262 determines desirable times to administer various therapies. For example, the detector 262 may detect the occurrence of an arrhythmia and automatically control the application of an appropriate electrical shock therapy to the heart aimed at terminating the detected arrhythmia. To this end, the controller circuit 260 further controls a shocking circuit 273 by way of a control signal 279. The shocking circuit 273 generates shocking pulses that are applied to the heart 105 of the patient through at least two shocking electrodes. The shocking pulses may be selected from the LA coil electrode 128, the RV coil electrode 136, and/or the SVC coil electrode 138 (all three electrodes shown in FIG. 1). The CAN 140 may act as an active electrode in combination with the RV coil electrode 136, or as part of a split electrical vector using the SVC coil electrode 138 or the LA coil electrode 128 (e.g., with the RV coil electrode 136 as a common electrode).

The controller circuit 260 may additionally include a morphology detector 264. The arrhythmia detector 262 and/or morphology detector 264 may be implemented in hardware as part of the controller circuit 260, or as software/ firmware instructions programmed into the system 100 and executed on the controller circuit 260 during certain modes of operation.

The pulse generator 270, 272 deliver a pacing sequence (e.g., CRT pacing) from the LV electrode combination designated for the first LVEC pacing site. The pulse generator 270, 272 deliver a first LV pacing pulse in the pacing sequence from the LV electrode combination. As noted herein, the LV electrode combination includes an adjacent pair of LV electrodes. The pulse generator 270, 272 is coupled to the switch 274 that sets the adjacent pair of LV electrodes as cathodes when delivering the LV pacing pulse. Optionally, the pulse generator 270, 272 and switch 274, controlled by the site designation module 269 designate adjacent at least first and second LV electrodes as cathodes to simultaneously deliver at least a first pacing pulse.

Depending upon the implementation, the aforementioned components (e.g., the negative hysteresis module 261) of the controller circuit 260 may be implemented in hardware as part of the controller circuit 260, or as software/firmware instructions programmed into the device and executed on the controller circuit 260 during certain modes of operation. In addition, the modules may be separate software modules or combined to permit a single module to perform multiple functions. In addition, although shown as being components of the controller circuit 260, some or all of the components/modules described above may be implemented separately from the controller circuit 260 using application specific integrated circuits (ASICs) or the like.

The controller circuit 260 is further coupled to a memory 294 by a suitable data/address bus 296. The programmable operating parameters used by the controller circuit 260 are stored in the memory 294 and modified, as required, in order to customize the operation of IMD 100 to suit the needs of a particular patient. Such operating parameters define, for example, the amplitude or magnitude of the generated pacing pulses, wave shape, pulse duration, the measurement cycle, the BiV pacing cycle, and/or the like. Other pacing parameters may include base rate, rest rate, and/or circadian base rate. The memory 294 further may store one or more parameters that are used to define adjustments and/or of the CRT pacing, such as the intrinsic AV conduction interval 314, the paced AV delay 316, the start 306 of the intrinsic atrial conduction 308, the intrinsic ventricular conduction 303, and/or the like.

Optionally, the operating parameters of the implantable IMD 100 may be non-invasively programmed into the memory 294 through a radio frequency (RF) circuit 201 in communication with an external device such as an external programmer device 204 or a bedside monitor 202 (e.g., a programmer, trans-telephonic transceiver, or a diagnostic system analyzer, and/or the like). The RF circuit 201 may support a particular wireless communication protocol while communicating with the external programmer device 201 or the bedside monitor 202, such as Bluetooth low energy, Bluetooth, ZigBee, Medical Implant Communication Service (MICS), or the like. Protocol firmware corresponding to the wireless communication protocol may be stored in memory 194, which is accessed by the microcontroller 160. The protocol firmware provides the wireless protocol syntax for the controller circuit 260 to assemble data packets, establish communication links 203, and/or partition data received from the external programmer device 201 or the bedside monitor 202.

Optionally, the RF circuit 201 may support telemetry communication. For example, the RF circuit 201 may be activated by the controller circuit 260 through a control signal 206. The RF circuit 201 may allow IEGMs and status information relating to the operation of IMD 100 (contained in the controller circuit 260 or the memory 294) to be sent to the external device 202, and vice-versa, through the established communication link 203. An internal warning device 221 may be provided for generating perceptible warning signals to a patient and/or caregiver via vibration, voltage, or other methods.

The IMD 100 may further include an accelerometer or other physiologic sensor 208. The physiologic sensor 208 is commonly referred to as a "rate-responsive" sensor because it may be used to adjust the pacing stimulation rate according to the exercise state (e.g., heart rate) of the patient. However, the physiological sensor 208 may further be used to detect changes in cardiac output, changes in the physiological condition of the heart, and/or diurnal changes in activity (e.g., detecting sleep and wake states and arousal from sleep). Accordingly, the controller circuit 260 may respond to such changes by adjusting the various pacing parameters (such as rate, interatrial delay, interventricular pacing delay, AV delay, negative hysteresis delta, etc.) at which the pulse generators 270 and 272 generate stimulation pulses. While shown as being included within IMD 100, it is to be understood that the physiologic sensor 208 may also be external to the IMD 100. Optionally, the physiologic sensor 208 may still be implanted within or carried by the patient. A common type of rate responsive sensor 208 is an activity sensor incorporating an accelerometer or a piezoelectric crystal, which is mounted within the housing/case 140 of the IMD 100. Other types of physiologic sensors 208 are also known, such as sensors that sense the oxygen content of blood, respiration rate and/or minute ventilation, pH of blood, ventricular gradient, stroke volume, cardiac output, contractility, and the like.

The IMD 100 additionally includes a battery 210, which provides operating power to all of the circuits shown in FIG. 2. The makeup of the battery 210 may vary depending on the capabilities of IMD 100. If the system only provides low voltage therapy (e.g., for repetitive pacing pulses), a lithium iodine or lithium copper fluoride cell may be utilized. For a IMD that employs shocking therapy, the battery may be configured to be capable of operating at low current drains for long periods and then providing high-current pulses (for capacitor charging) when the patient requires a shock pulse. The battery 210 may also be configured to have a predictable discharge characteristic so that elective replacement time can be detected.

As further shown in FIG. 2, the IMD 100 has an impedance measuring circuit 212, which is enabled by the controller circuit 260 via a control signal 215. Uses for an impedance measuring circuit 212 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 212 is coupled to the switch 274 so that any desired electrode may be used.

The above described IMD 100 was described as an exemplary IMD. One of ordinary skill in the art would understand that one or more embodiments herein may be used with alternative types of implantable medical devices. Accordingly, embodiments should not be limited to using only the above described device 100.

Figure 4:
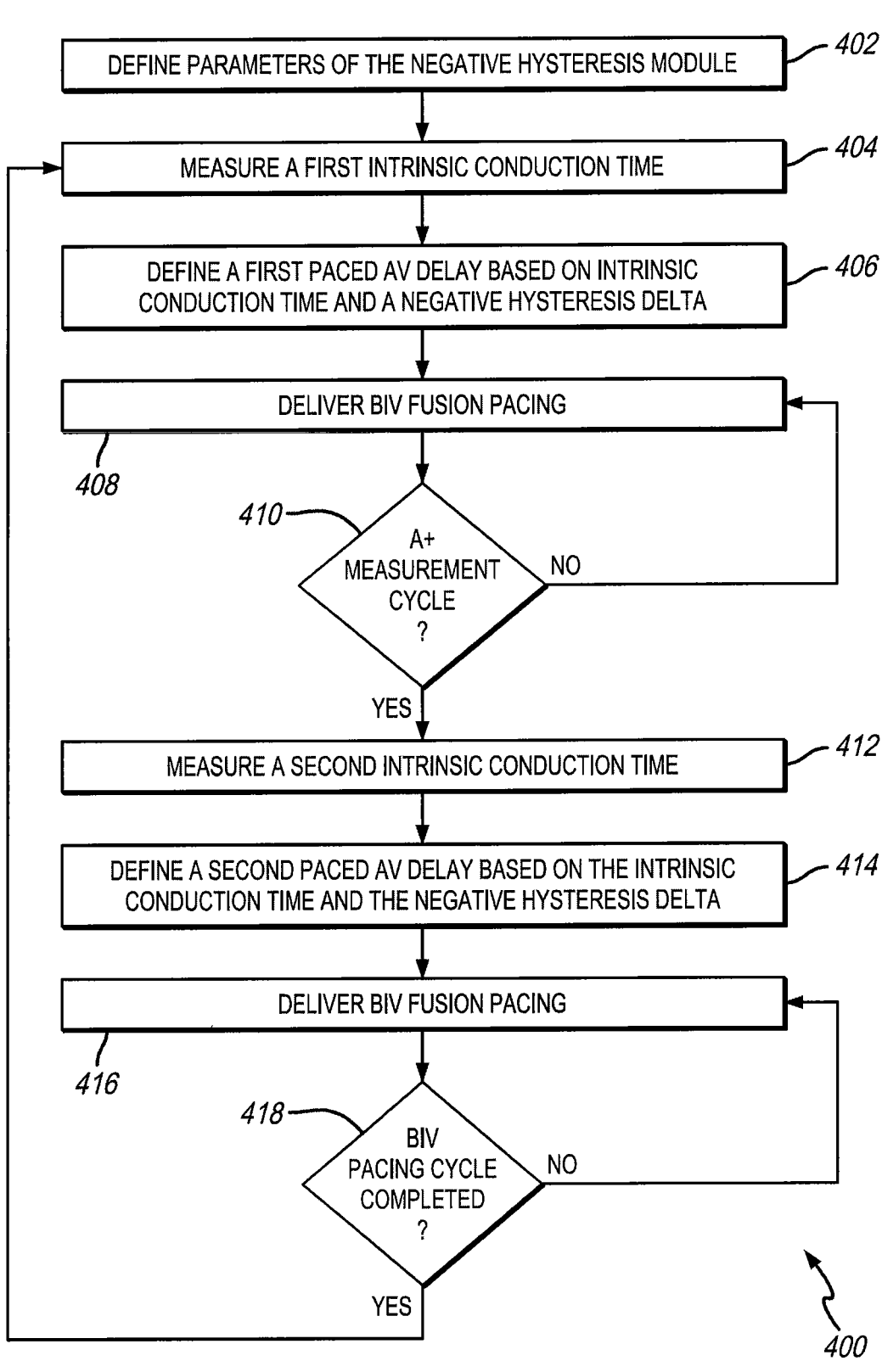
FIG. 4 illustrates a flow chart of a method for bi ventricular fusion pacing, according to an embodiment.

FIG. 4 illustrates a flowchart of a method 400 for rate adaptive BiV fusion pacing. The method 400 may be implemented as a software algorithm (e.g., the negative hysteresis module 261), package, or system that directs one or more hardware circuits or circuitry to perform the actions described herein. For example, the operations of the method 400 may represent actions to be performed by one or more circuits (e.g., the controller circuit 260) that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic of the.

Beginning at 402, the controller circuit 260 may define parameters of the negative hysteresis module 261. Optionally, the controller circuit 260 may define the parameters of the negative hysteresis module 251 based on instructions received from the external programmer 204 operated by a clinician (e.g., doctor, nurse). For example, a clinician may define or select the parameters to customize the BiV fusion pacing delivered by the IMD 100 via the communication link 203 based on the patient. In various embodiments, the clinician may define the parameters of the negative hysteresis module 261 during implantation and/or a medical examination of the IMD 100 based on echocardiography (ECHO) optimization, measurement of a QRS complex, and/or the like.

The parameters may include operational parameters of the negative hysteresis module 261 that are utilized by the negative hysteresis module 261 for the timing of the BiV fusion pacing. For example, the controller circuit 260 may define a default paced AV delay, the negative hysteresis delta, a minimum AV delay, interventricular pacing delay, a number of cycles for the measurement cycle, a number of cycles for a BiV pacing cycle, and/or the like. The default paced AV delay may be a length of time that allows for intrinsic conduction of the heart 105. For example, the default paced AV delay may be configured (e.g., greater than 200 milliseconds) to delay the IMD 100 from delivering the BiV fusion pacing to allow the intrinsic ventricular conduction of the heart 105 to preempt the BiV fusion pacing.

The minimum AV delay may be a minimum length of time that the negative hysteresis module 261 may set the paced AV delay. For example, the minimum AV delay may be defined at 100 milliseconds, and a negative hysteresis delta may be defined at 50 milliseconds. The negative hysteresis module 261 measures an intrinsic AV conduction interval of 140 milliseconds. As described in connection with Equation 1, the negative hysteresis module 261 may calculate a paced AV delay of 90 milliseconds by subtracting the negative hysteresis delta, of 50 milliseconds, from the intrinsic AV conduction interval, of 140 milliseconds. The negative hysteresis module 261 would compare the calculated paced AV delay with the minimum AV delay. If the calculated paced AV delay is less or shorter than the minimum AV delay, the negative hysteresis module 261 may set the paced AV delay as the minimum AV delay. By way of example, the minimum AV delay may range from 25 milliseconds to 120 milliseconds.

The interventricular pacing delay may correspond to a difference in time between BiV fusion pacing delivered to the LV 116 and the BiV fusion pacing delivered to the RV 114. For example, the interventricular pacing delay may range from 5 milliseconds to 80 milliseconds. The interventricular pacing delay may be adjusted to customize the BiV fusion pacing pulses to the patient. For example, the interventricular pacing delay may be configured to occur subsequent to an intrinsic conduction of the RV 114.

At 404, the controller circuit 260 measures a first intrinsic conduction time. The first intrinsic conduction time may be a first intrinsic AV conduction interval 520 of the heart 105. For example, in connection with FIG. 5, the controller circuit 260 or the negative hysteresis module 261 may calculate an intrinsic AV conduction interval 520 based on measurements received by the atrial sensing circuit 282 and the ventricular sensing circuit 284 shown in FIG. 2.

Figure 5:
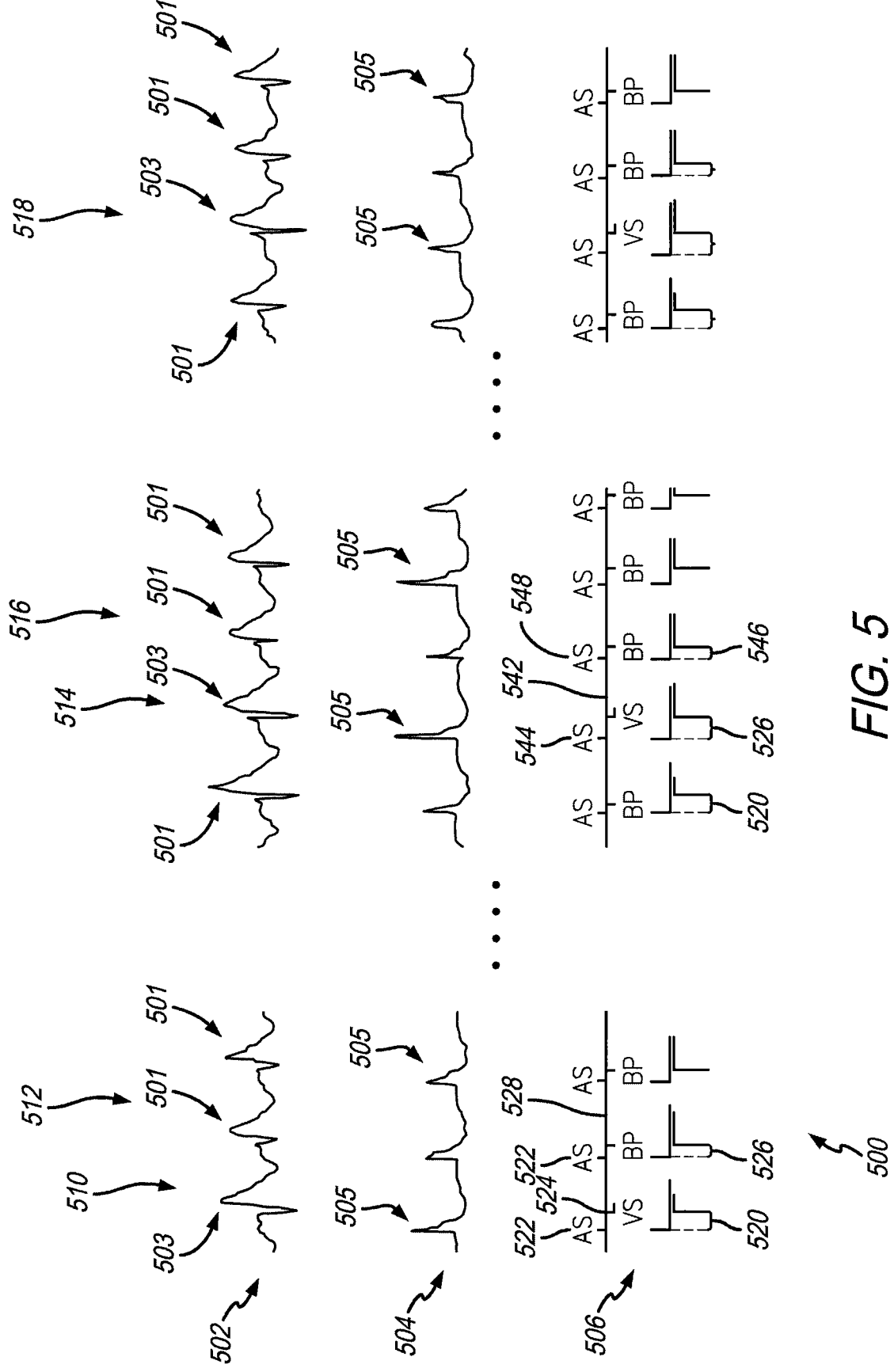
FIG. 5 illustrates electrocardiography and pacing delay data, according to an embodiment.

FIG. 5 illustrates electrocardiography and pacing delay data 500, in accordance with an embodiment. The data 500 may have been acquired by the IMD 100 during a series of cycles. The illustrated electrocardiography data includes a heart electrocardiogram 502 and an atrial electrocardiogram 504 acquired by the atrial sensing circuit 282 and/or the ventricular sensing circuit 284. The atrial electrocardiogram 504 illustrates a series of peaks 505, each corresponding to an intrinsic atrial conduction of the heart 105. A start of each peak 505 of the atrial electrocardiogram 504 may define a start of a cycle (e.g., 510, 512, 514, 516, 518) of the IMD 101. The heart electrocardiogram 502 includes peaks 503 that include intrinsic ventricular conduction, and peaks 501 in response to BiV fusion pacing.

Timing data of the intrinsic atrial conductions and the intrinsic ventricular conduction, for example determined by the negative hysteresis module 261, are illustrated in the pacing delay data 506. The intrinsic atrial depolarization is represented by the AS indicator 522. The intrinsic ventricular depolarization is represented by the VS indicator 524.

The negative hysteresis module 261 may measure the first intrinsic conduction time, such as the intrinsic AV conduction interval 520, during an initial cycle 510 of the IMD 100. During the initial cycle 510 the negative hysteresis module 261 may utilize the default paced AV delay defined at 402. The default paced AV delay may be configured to be longer than the intrinsic ventricular conduction time of the patient. For example, the intrinsic ventricular conduction of the patient occurs within or during the default paced AV delay. The negative hysteresis module 261 may measure a peak 503 that includes an intrinsic ventricular depolarization, which is represented by the indicator 524.

The negative hysteresis module 261 may calculate the first intrinsic AV conduction interval 520 based on when the intrinsic atrial depolarization and the intrinsic ventricular depolarization occurs. The first intrinsic AV conduction interval 520 represents an amount of time from the intrinsic atrial depolarization, occurring at the indicator 522, to the intrinsic ventricular depolarization occurring at the indicator 524. For example, the intrinsic AV conduction interval 520 corresponds to a length of time between the indicator 522 and the indicator 524.

At 406, the controller circuit 260 defines a first paced AV delay 526 based on the first intrinsic conduction time 520 and a negative hysteresis delta. The first paced AV delay 526 defines when the IMD 100 delivers BiV fusion pacing, represented by BP indicator 528, after or subsequent to the intrinsic atrial conduction (e.g., the AS indicator 522). The first paced AV delay 526 is calculated or defined by the negative hysteresis module 261 based on the first intrinsic AV conduction interval 520 and the negative hysteresis delta. As shown in Equation 1, the negative hysteresis module 261 may determine the first paced AV delay 526 by reducing or subtracting the intrinsic AV conduction interval 520 by the negative hysteresis delta. For example, the negative hysteresis module 261 may determine the intrinsic AV conduction interval 520 is 140 milliseconds. The negative hysteresis module 261 may subtract from the intrinsic AV conduction interval 520 the negative hysteresis delta corresponding to, for example, 50 milliseconds. Based on the AV conduction interval 520 and the negative hysteresis delta, the negative hysteresis module 261 may define the first paced AV delay 526 to be 90 milliseconds.

At 408, the IMD 100 delivers BiV fusion pacing to the heart 105. The BiV fusion pacing may include sequences of pacing pulses (e.g., one or more pacing pulses) generated by the pulse generators 270, 272 and routed by the switch 274 (shown in FIG. 2) to the LV 116 and the RV 114. For example, the controller circuit 260 detects a beginning of a cycle 512 at the intrinsic atrial conduction, shown as the AS indicator 522. After the first paced AV delay 526, corresponding to an end of the cycle 512, the controller circuit 260 may instruct the pulse generator 270 to generate a sequence of pulses for delivery to the RV lead 130, and instruct the pulse generator 272 to generate a sequence of pulses for delivery to the LV lead 124.

At 410, the controller circuit 260 determines whether the measurement cycle 514 is reached. The measurement cycle 514 may occur after a predetermined number of cycles subsequent or after the initial cycle 510. The controller circuit 260 may continually deliver the BiV fusion pacing to the heart 105, at 408, until the measurement cycle 514. For example, the controller circuit 260 may count a number of cycles after the initial cycle 510 until the measurement cycle 514 is reached, starting at the intrinsic atrial depolarization represented by an AS indicator 544.

When the measurement cycle is reached, at 412, the controller circuit 260 measures a second intrinsic conduction time. For example, the controller circuit 260 may adjust to the default paced AV delay to allow the intrinsic ventricular conduction, represented as a VS indicator 542, to pre-empt the BiV fusion pacing (e.g., the intrinsic ventricular conduction of the patient occurs within or during the default paced AV delay). The negative hysteresis module 261 may calculate the second intrinsic AV conduction interval 540 based on when the intrinsic atrial conduction, at the indicator 544, and the intrinsic ventricular conduction occurs at the indicator 542.

At 414, the controller circuit 260 adjusts the paced AV delay to correspond to a second paced AV delay 546 based on the intrinsic conduction time and the Negative Hysteresis delta. For example, the second paced AV delay 546 is calculated or defined by the negative hysteresis module 261 based on the second intrinsic AV conduction interval 540 and the negative hysteresis delta. As shown in Equation 1, the negative hysteresis module 261 may determine the second paced AV delay 546 by reducing or subtracting the second intrinsic AV conduction interval 540 by the negative hysteresis delta. For example, the negative hysteresis module 261 may adjusts the paced AV delay to be the second intrinsic AV conduction interval 540 is 160 milliseconds, and subtract from the intrinsic AV conduction interval 520 the negative hysteresis delta of, for example, 50 milliseconds. Based on the second AV conduction interval 540 and the negative hysteresis delta, the negative hysteresis module 261 defines the second paced AV delay 546 to be 110 milliseconds.

At 416, the IMD 100 delivers BiV fusion pacing to the heart 105. For example, the controller circuit 260 detects a beginning of a cycle 516 at the intrinsic atrial conduction, shown as the AS indicator 548. After the second paced AV delay 546, corresponding to an end of the cycle 516, the controller circuit 260 may instruct the pulse generator 270 to generate a sequence of pulses for delivery to the RV lead 130, and the pulse generator 272 to generate a sequence of pulses for delivery to the LV lead 124.

At 418, the controller circuit 260 determines whether the BiV pacing cycle is completed. The BiV pacing cycle may include a predetermined number of cycles subsequent or after the measurement cycle 514. The controller circuit 260 may continually deliver the BiV fusion pacing to the heart 105, at 416, until a consecutive number of cycles of the BiV pacing cycle is reached. For example, the controller circuit 260 may count a number of cycles after the measurement cycle 514 until the predetermined number of cycles of the BiV pacing cycle is reached.

When the BiV pacing cycle is complete, the controller circuit 260 may continually repeat the method 400. For example, the controller circuit 260 may return to 404 to measure an intrinsic conduction time for a second initial cycle 518.

Figure 6:
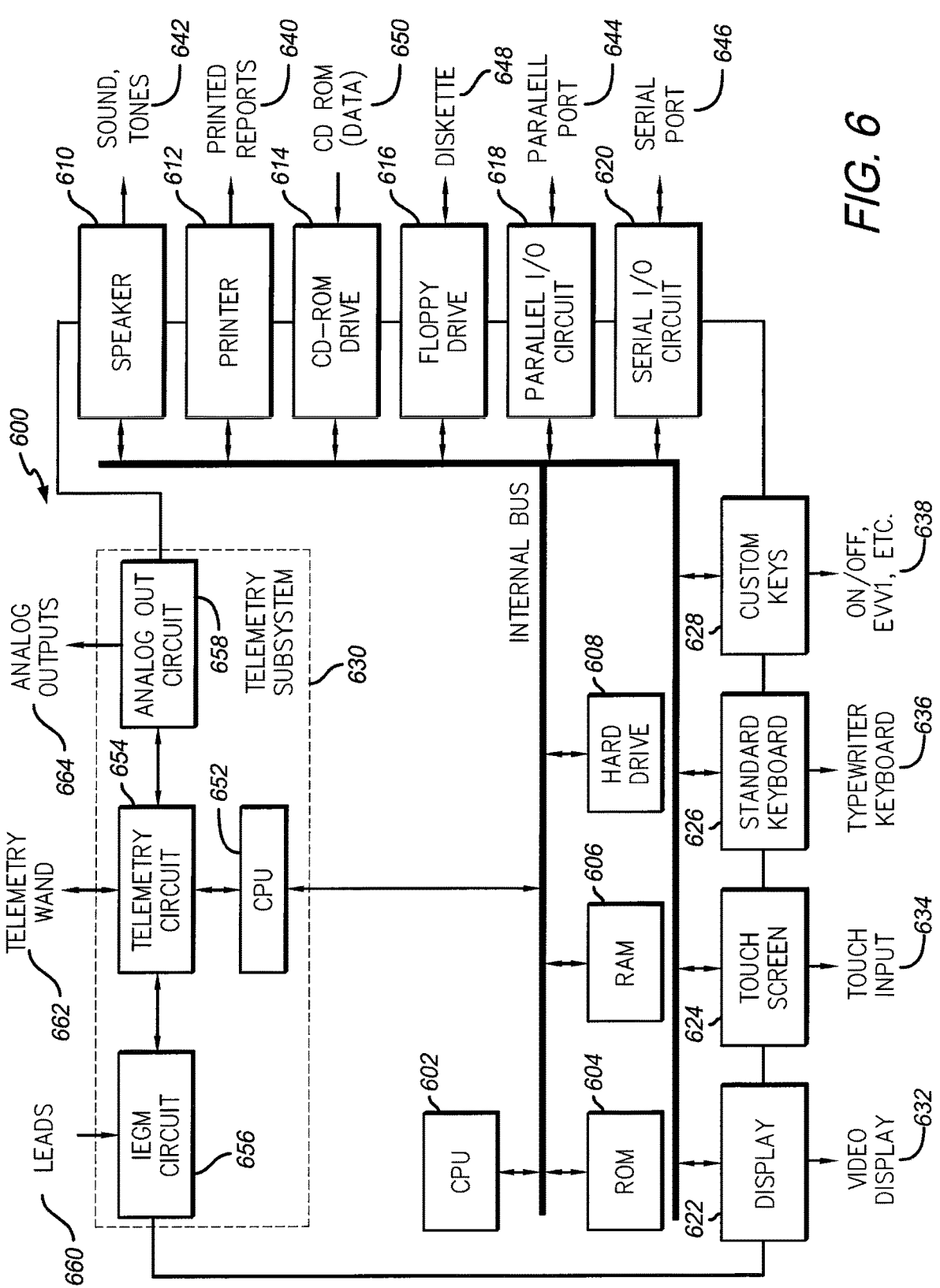
FIG. 6 illustrates a functional block diagram of an external device that is operated in accordance with the processes described herein.

FIG. 6 illustrates a functional block diagram of an external device 600 that is operated in accordance with the processes described herein and to interface with the implantable medical device 100 as shown in FIGS. 1 and 2 and described herein. The external device 600 may be the external programmer device 104 shown in FIG. 2. The external device 600 may take the form of a workstation, a portable computer, an IMD programmer, a PDA, a cell phone, and/or the like. The external device 600 includes an internal bus that connects/interfaces with a Central Processing Unit (CPU) 602, ROM 604, RAM 606, a hard drive 608, a speaker 610, a printer 612, a CD-ROM drive 614, a floppy drive 616, a parallel I/O circuit 618, a serial I/O circuit 620, a display 622, a touch screen 624, a standard keyboard 626, custom keys 628, and/or a telemetry subsystem 630. The internal bus is an address/data bus that transfers information between the various components described herein. The hard drive 608 may store operational programs as well as data, such as waveform templates, for the CRT pacing.

The CPU 602 includes a microprocessor, a micro-controller, and/or equivalent control circuitry, designed specifically to control interfacing with the external device 600 and with the IMD 100. The CPU 602 may include RAM or ROM memory, logic and timing circuitry, state machine circuitry, and/or I/O circuitry to interface with the IMD 100. The ROM 604, RAM 606 and/or hard drive 608 store program instructions that one executed by one or more processors (e.g., the CPU 602) to perform the operations described herein.

The display 622 may be connected to a video display 632. The display 622 displays various forms of information related to the processes described herein. The touch screen 624 may display graphic user information (GUI) relating to the IMD 100. For example, the GUI may provide a plurality of candidate parameters the user may select from to define the parameters for the negative hysteresis module 260. The touch screen 624 accepts a user's touch input 634 when selections are made. The keyboard 626 (e.g., a typewriter keyboard 636) allows a user to enter data to displayed fields, as well as interface with the telemetry subsystem 630. Furthermore, custom keys 628 turn on/off 638 (e.g., EVVI) the external device 600. The printer 612 prints copies of reports 640 for a physician to review or to be placed in a patient file, and speaker 610 provides an audible warning (e.g., sounds and tones 642) to the user. The parallel I/O circuit 618 interfaces with a parallel port 644. The serial I/O circuit 620 interfaces with a serial port 646. The floppy drive 616 accepts diskettes 648. Optionally, the floppy drive 616 may include a USB port or other interface capable of communicating with a USB device such as a flash memory stick. The CD-ROM drive 614 accepts CD ROMs 650. The CD-ROM drive 614 optionally may include a DVD port capable of reading and/or writing DVDs.

The telemetry subsystem 630 includes a central processing unit (CPU) 652 in electrical communication with a telemetry circuit 654, which communicates with both an IEGM circuit 656 and an analog out circuit 658. The IEGM circuit 656 may be connected to leads 660. The IEGM circuit 656 is also connected to the implantable leads 120, 124 and 130 (shown in FIG. 1) to receive and process IEGM cardiac signals. Optionally, the IEGM cardiac signals sensed by the leads 120, 124 and 130 may be collected by the IMD 100 and then wirelessly transmitted to the telemetry subsystem 630 input of the external device 600.

The telemetry circuit 654 is connected to a telemetry wand 662. The analog out circuit 658 includes communication circuits to communicate with analog outputs 664. The external device 600 may wirelessly communicate with the IMD 100 and utilize protocols, such as Bluetooth, GSM, infrared wireless LANs, HIPERLAN, 3G, 4G, satellite, as well as circuit and packet data protocols, and the like. Alternatively, a hard-wired connection may be used to connect the external device 600 to the IMD 100.

The block diagrams of embodiments herein illustrate various blocks that may be labeled "module", "unit" and the like. It is to be understood that the modules, units, etc. represent circuits that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hard-wired to perform the functions described herein. Optionally, the hardware may include electronic circuits that include and/or are connected to one or more logic-based devices, such as microprocessors, processors, controllers, or the like. Optionally, the modules, units, etc. may represent processing circuitry such as one or more field programmable gate array (FPGA), application specific integrated circuit (ASIC), or microprocessor. The modules, units, etc. in various embodiments may be configured to execute one or more algorithms to perform functions described herein. The one or more algorithms may include aspects of embodiments disclosed herein, whether or not expressly identified in a flowchart or a method.

The various methods as illustrated in the FIGS. and described herein represent exemplary embodiments of methods. The methods may be implemented in software, hardware, or a combination thereof. In various embodiments of the methods, the order of the steps may be changed, and various elements may be added, reordered, combined, omitted, modified, etc. Various steps of the method may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A method for bi-ventricular (BiV) fusion pacing, comprising:

providing a first electrode located in or proximate to a first ventricle;

providing a second electrode located in or proximate to a second ventricle;

delivering BiV fusion pacing that includes a first pulse delivered at the first electrode and a second pulse delivered at the second electrode based on a paced atrio-ventricular (AV) delay, wherein the first pulse is timed to be delivered concurrently with a patient's intrinsic ventricular conduction;

repeating the delivery of the first pulse and the second pulse for two or more cardiac cycles;

after repeating the delivering for the two or more cardiac cycles, measuring an intrinsic AV conduction interval; and adjusting the paced AV delay based on the measured intrinsic AV conduction interval and a negative hysteresis delta.

2. The method of claim 1, wherein the first ventricle corresponds to the right ventricle (RV) and first electrode is located in or proximate to the RV.

3. The method of claim 1, wherein the first ventricle corresponds to the left ventricle (LV) and first electrode is located in or proximate to the LV.

4. The method of claim 1, wherein the measuring of the intrinsic AV conduction interval is based on a plurality of intrinsic atrial conductions and corresponding intrinsic LV conductions.

5. The method of claim 1, wherein the measuring of the intrinsic AV conduction interval is based on a plurality of intrinsic atrial conductions and corresponding intrinsic RV conductions.

6. The method of claim 1, further comprising receiving an interventricular pacing delay as a user-defined programmable value, wherein the second pulse is delivered after the interventricular pacing delay relative to the first pulse, the interventricular pacing delay being selected from a plurality of candidate interventricular pacing delays.

7. The method of claim 1, wherein the providing includes providing first and second leads having the first and second electrodes, respectively.

8. The method of claim 1, wherein the measuring periodically or continually measures the intrinsic AV conduction interval and, based thereon, periodically or continually adjusts the paced AV delay to identify changes in at least one of heart rate, activity level of a patient, cardiac conduction status, or medication of the patient.

9. A system for bi-ventricular (BiV) fusion pacing, comprising:

a first electrode configured to be located in or proximate to a first ventricle;

a second electrode configured to be located in or proximate to a second ventricle;

a memory configured to store program instructions;

at least one processor that, when executing the program instructions, is configured to:

deliver BiV fusion pacing that includes delivering a first pulse at the first electrode and delivering a second pulse at the second electrode based on a paced atrio-ventricular (AV) delay, wherein the first pulse is timed to be delivered concurrently with a patient's intrinsic ventricular conduction;

repeat the delivery of the first pulse and the second pulse for two or more cardiac cycles;

after repeating the delivery for the two or more cardiac cycles, measure an intrinsic AV conduction interval; and adjust the paced AV delay based on the measured intrinsic AV conduction interval and a negative hysteresis delta.

10. The system of claim 9, wherein the first ventricle corresponds to the right ventricle (RV) and first electrode is configured to be located in or proximate to the RV.

11. The system of claim 9, wherein the first ventricle corresponds to the left ventricle (LV) and first electrode is located in or proximate to the LV.

12. The system of claim 9, wherein the at least one processor is configured to measure the intrinsic AV conduction interval based on a plurality of intrinsic atrial conductions and corresponding intrinsic LV conductions.

13. The system of claim 9, wherein the at least one processor is configured to measure the intrinsic AV conduction interval is based on a plurality of intrinsic atrial conductions and corresponding intrinsic RV conductions.

14. The system of claim 9, wherein the at least one processor is configured to: receive an interventricular pacing delay as a user-defined programmable value; deliver the second pulse after the interventricular pacing delay relative to the first pulse, the interventricular pacing delay being selected from a plurality of candidate interventricular pacing delays.

15. The system of claim 9, further comprising first and second leads having the first and second electrodes, respectively.

16. The system of claim 9, further comprising at least one implantable medical device that includes the at least one processor.

\* \* \* \* \*